United States Patent [19]
Hokanson

[11] 3,968,798
[45] July 13, 1976

[54] INCONTINENT PAD

[75] Inventor: Kenneth C. Hokanson, Greenwood, S.C.

[73] Assignee: Parke, Davis & Company, Detroit, Mich.

[22] Filed: July 3, 1975

[21] Appl. No.: 592,962

[52] U.S. Cl............................. 128/284; 128/287; 128/290 P; 128/290 R; 128/296
[51] Int. Cl.² .................. A61F 13/16; A61F 13/18
[58] Field of Search............. 128/284, 287, 290 W, 128/290 P, 290 R, 296; 156/201

[56] References Cited
UNITED STATES PATENTS

| | | | |
|---|---|---|---|
| 2,896,626 | 7/1959 | Voigtman | 128/287 |
| 3,395,708 | 8/1968 | Hervey et al. | 128/284 |
| 3,658,064 | 4/1972 | Pociluyko | 128/287 |
| 3,665,923 | 5/1972 | Champaigne | 128/290 W |
| 3,693,621 | 9/1972 | Jarusik et al. | 128/287 |
| 3,848,594 | 11/1974 | Buell | 128/284 |
| 3,868,287 | 2/1975 | Lewyckyj | 156/201 |
| 3,888,257 | 6/1975 | Cook et al. | 128/296 |

*Primary Examiner*—Aldrich F. Medbery
*Attorney, Agent, or Firm*—David B. Ehrlinger; George M. Richards; Stephen Raines

[57] ABSTRACT

A disposable incontinent pad such as an adult diaper or the like is provided comprising a fluid absorbent matrix with facing and backing sides, a facing sheet, and a water-impervious backing sheet in layered relation having the matrix infolded at its lateral edges onto the facing side in a C-fold configuration with the backing sheet overlapping the fold lines onto the facing sheet such that the pad when worn in a holder garment in fluid-absorbing relation with the body is resistant to lateral run-off of body fluid.

7 Claims, 4 Drawing Figures

U.S. Patent  July 13, 1976  3,968,798
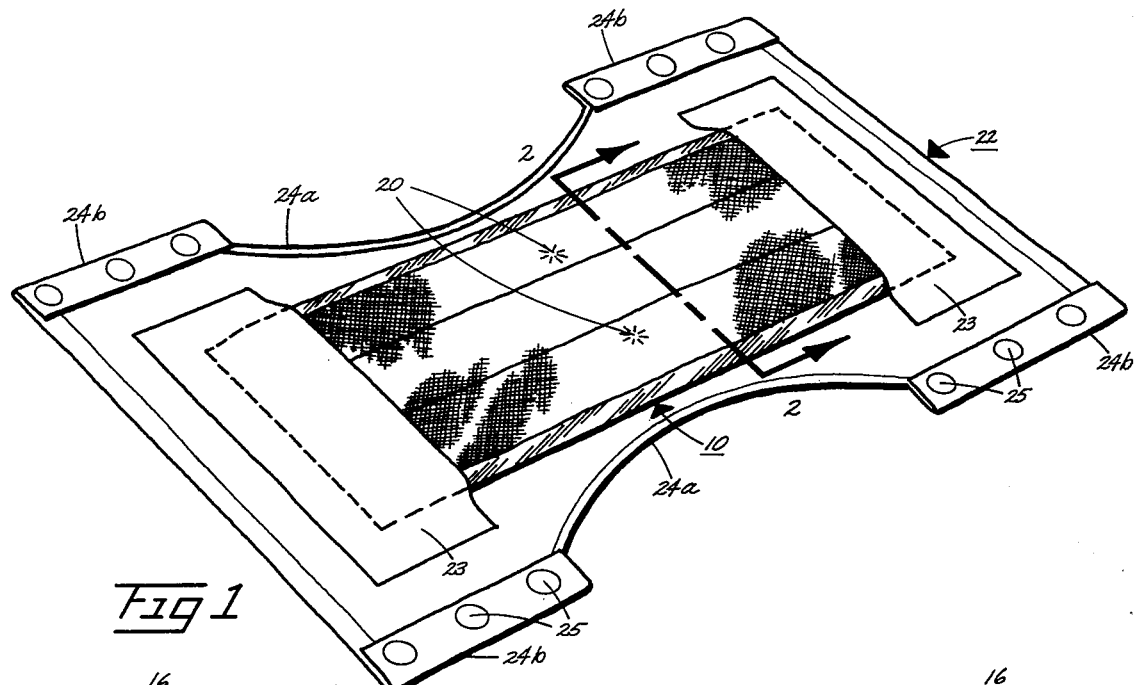
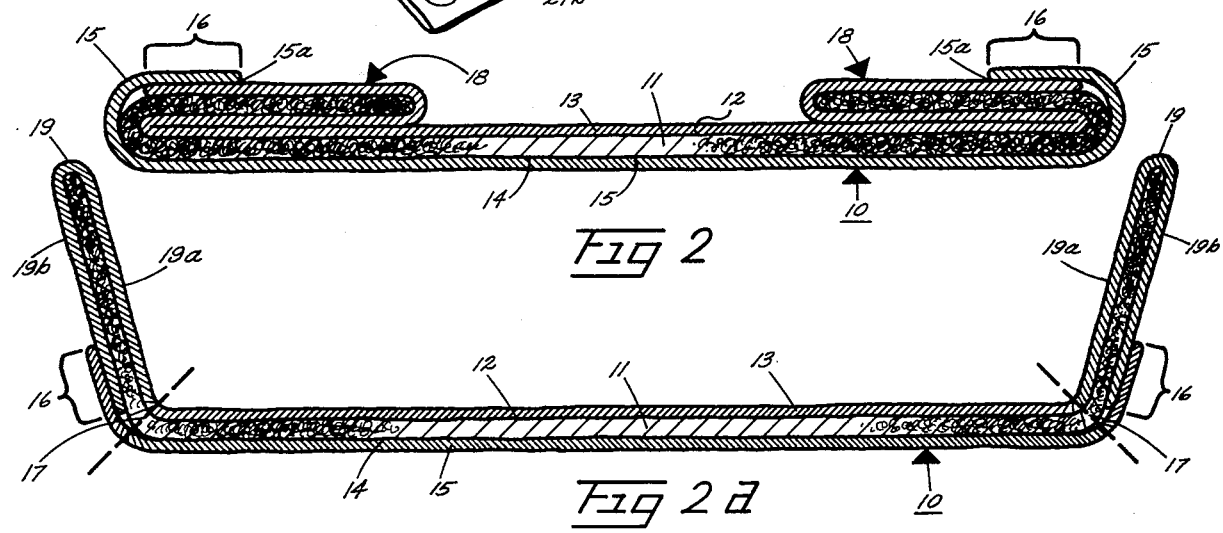
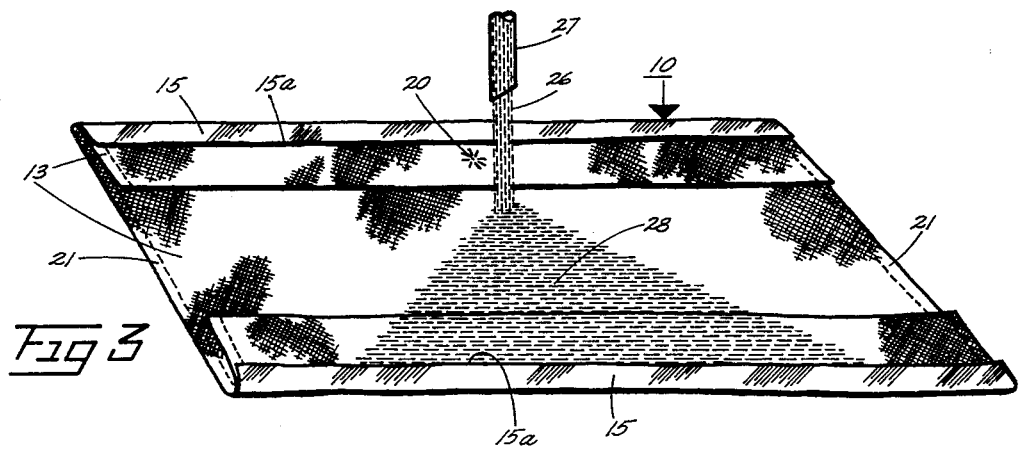

INCONTINENT PAD

SUMMARY AND DETAILED DESCRIPTION

This invention relates to an improved incontinent pad adapted to be worn in a fitted holder garment, belt, panty, or the like. More particularly, the invention relates to an improved incontinent pad which when worn in a holder garment is per se resistant to lateral run-off of body fluid.

Prior art absorbent incontinent pads and diapering systems are of two types:

1. A total system in which the absorbent material and water-impervious barrier or backing are incorporated in a single functional unit, optionally with a box pleat or conventional C-fold to enable fitting at the waist; and
2. A two-part system including a disposable absorbent pad, cloth diaper or the like used with a water-impervious holder panty tie-on or the like to protect the outer clothing, bed linens, etc.

In the total system the unit prior to usage is in a folded condition which for use must be flared out at the ends of the diaper for attachment by pinning or taping. The flared ends of the article must of necessity be covered with a water-impervious barrier to insure the desired protection against soiling. The two-part system, on the other hand, purposely avoids use of a water-impervious backing for the pad since the other component of the two-part system, the plastic panty or holder, serves the function of a moisture barrier.

The usual difficulty with these prior systems is that they are uncomfortable due to bulk, stiffness, etc.; or have a high exposure of plastic to skin surface; or are uneconomic; etc.

It therefore is an object of the present invention to provide an improved incontinent pad which meets requirements for economy and can be manufactured by conventional machine technics.

Another object of the invention is to provide an article of the kind described which affords fast fluid uptake, high capacity under pressure, and relative freedom from lateral run-off of body fluid.

Yet another object is to provide article means for management of incontinence which accomplishes the foregoing advantages and yet minimizes discomfort, adverse skin contact, and the like.

These and other objects, purposes and advantages of the invention will be seen from the following description and the accompanying drawing in which:

FIG. 1 is a view in perspective of an incontinent pad assembled in a holder;

FIG. 2 is a cross-section of the pad taken on line 2—2 of FIG. 1;

FIG. 2a is a similar view showing the manner of constructing the pad; and

FIG. 3 illustrates a pad under test conditions being subjected to fluid flow against a lateral edge of the pad.

Referring to FIG. 1, which illustrates a preferred form of the invention, an absorbent pad 10 is provided in a holder garment or panty 22, which per se may be in conventional form with opposed pockets 23 maintaining the pad in axial alignment with the holder. The holder includes cutaway edge portions 24a to accommodate close fitting at the legs. Also on the side edges 24b securing means 25 are provided for joining and fastening the front and back side edges for attachment to the waist.

As shown in the cross-section of FIG. 2, the pad 10 includes a matrix 11 having its facing side 12 covered with a facing sheet 13 and its backing side 14 partly covered with a backing sheet 15. The matrix is suitably fabricated of material having a high capacity for absorbing body fluid, one preferred embodiment being a fiberized wood pulp batt interposed between wadding sheets or tissue layers. The body of the matrix can be loaded with water-imbibing substances such as hydrocolloid polymer particles to enhance the water-absorbing capacity of the matrix. The matrix is infolded at two fold lines 17 to provide flaps 18. The facing sheet 13 overlaps the lateral edges 19 of the flaps providing inner and outer faces 19a and 19b for the flaps. The backing sheet 15 overlaps the facing sheet in two parallel sealing zones 16, thus forming an envelope enclosing the matrix.

The pad 10 can conveniently be made by endless conveyor web handling means. In one preferred embodiment the matrix is formed from a moving web of fiberized wood pulp held between wadding layers. The moving matrix web is laid down on its facing side onto a moving facing sheet web which is then overlapped onto the backing side, as illustrated in FIG. 2a. The backing sheet in a like moving web is then brought into layered relation (as illustrated in FIG. 2a), overlapping the lateral edges of the facing in parallel sealing zones 16. The layers are laminated together with suitable adhesive means and the flaps 18 are then formed by infolding at fold lines 17 to provide the cross-section illustrated at FIG. 2. The folds are held in place with a suitable adhesive at adhesive spots 20. The ends of the pad 10 are finally cut from the moving composite web and provided with full end seals 21 in conventional fashion.

In regard to efficiency and cost, the incontinent pad of the present invention provides unexpected advantage over conventional configurations such as a regular diaper (coextensive pad and facing, overlapping backing), a diaper pad (pad with facing sleeve but lacking a plastic barrier), a box-pleated diaper, and a regular C-folded diaper. The advantage can be shown by a simple test comparison. In this comparison, each article, specially made with identical materials (nonwoven rayon facing, wood fluff/wadding layered absorbent and, where applicable, impervious 1 mil polyethylene plastic film backing) and with equal amounts of absorbent material, was tested for lateral run-off. The test, illustrated in FIG. 3 showing the leak-proof characteristics of the present incontinent pad, is carried out with the pad held at a 45° angle exposed to flooding. Water 26 in a 50 ml. quantity colored with dye is released at a constant rate lasting 10 seconds through a delivery tube 27 onto the pad surface where it distributes in a fan-shape 28, as illustrated. The results typically were as follows:

| Disposable Diaper Type | Relative Area of Plastic Film/Diaper | Relative Plastic Film-Body Contact | Lateral Run-Off |
|---|---|---|---|
| Regular Diaper | 1.69 | 1.00 | some |
| Regular Diaper Pad | — | — | severe |
| Box-Pleated Diaper | 1.69 | 1.00 | none |
| Regular Diaper, C-folded | 1.69 | 3.8 | none |
| Diaper of FIG. 3 | 1.00 | 1.00 | none |

These results show that the diaper pad of the invention was at least equal to the compared functional constructions with respect to the listed characteristics. However, the results show that the present diaper pad was unexpectedly better than the others in at least one of three characteristics: quantity of plastic film per unit, area of exposure to plastic, and protection against lateral run-off.

The regular diaper failed to hold the first release of water. The water struck the surface and ran off. About 10–15 ml. was lost before the absorbent material started to absorb, after which practically all liquid was drawn into the diaper.

For the regular diaper pad, not only did the liquid run off initially but it also drained from the pad throughout the test.

By comparison, the box-pleated diaper, the regular C-folded diaper, and the diaper of the present invention all retained the liquid under the test conditions with no run-off or drainage. Thus, the pad of the present invention absorbed and held the same quantity of fluid as the box-pleated diaper or the regular C-folded diaper.

The incontinent pad of the present invention has therefore several advantages over the other configurations:

1. Smaller area of plastic-to-body contact than the regular C-folded diaper;
2. Less plastic material than all but the diaper pad;
3. Less bulk at the lateral edges—only two layers of absorbent material whereas the box-pleated diaper has three;
4. Retains liquid with the least amount of plastic.

The component materials of the present incontinent pad can be selected from a wide variety of available options based on recognized requirements for low cost, efficiency, biodegradability, etc. The absorbent matrix, for example, can be cellulosic in content and can be fortified, if desired, with agents to accommodate flooding, etc., such as the water-imbibing polymer means indicated above. The facing material preferably is a cover material which is non-absorbent per se but which readily transmits water and feels dry to the touch. The water-impervious backing material preferably is a resilient polymeric film or web. A preferred adult diaper for purposes of the invention typically measures 14 inches wide (unfolded, and 8 inches folded width) by about 21 inches long and consists of a 1 mil polyethylene film backing sheet (about 9½ inches wide), an 18 gram per square yard nonwoven rayon cover (21 inches wide), and a matrix containing about 30 to 40 grams of fiberized bleached wood pulp between two layers of 10 pound creped cellulose tissue or wadding. Another preferred embodiment is the diaper described in which the body of the matrix (and preferably the middle portion thereof) is loaded with a uniform dispersion of water-imbibing hydrocolloid polymer particles. Preferably, the polymer has a water-absorbing capacity of at least 50 parts of water per part by weight of polymer, such as described in U.S. Pat. No. 3,888,257, and preferably from 2 to 10 grams of polymer are used in the matrix.

While the invention in an incontinent pad or the like has been described in detail, it will be realized by those skilled in the art that wide variation in such detail can be made without departing from the spirit of the invention as claimed below. It is intended that the claims which follow should be interpreted to cover the invention as described and any such variation.

I claim:

1. A disposable nursing or incontinent pad or the like adapted to absorb body fluids, comprising in layered relation:
   a rectilinear absorbent matrix having a facing side and a backing side,
   a facing sheet, and
   a water-impervious backing sheet,
   the matrix being sealingly enveloped within the facing and backing sheets and having its lateral edges infolded onto the facing side in a C-fold configuration to provide two spaced apart infolded flaps and a middle portion between the fold lines,
   the facing sheet being wider than the matrix and extending over the facing side of the middle portion and the outer and inner faces of each of the infolded flaps,
   the backing sheet being narrower than the matrix and overlapping the facing sheet on said outer face such that the pad in fluid absorbing relation with the body is resistant to lateral run-off of fluid.

2. A disposable pad according to claim 1 in combination with holder means adapted to be worn.

3. A disposable pad according to claim 1 wherein the matrix comprises fiberized wood pulp.

4. A disposable pad according to claim 3 wherein the middle portion of the matrix contains a uniform dispersion of hydrocolloid polymer particles.

5. A disposable pad according to claim 4 wherein the matrix comprises cellulose tissue layers.

6. A disposable pad according to claim 1 wherein the backing sheet overlaps the facing sheet in two sealing zones each closely adjacent to the fold lines such that in fluid absorbing relation with the body contact in the flap area between the skin and the backing sheet is minimized.

7. A disposable pad according to claim 6 wherein the backing sheet is a water-impervious polymeric film.

* * * * *